United States Patent [19]

Haber et al.

[11] Patent Number: 5,147,323
[45] Date of Patent: Sep. 15, 1992

[54] MULTIPLE CARTRIDGE SYRINGE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 667,319

[22] Filed: Mar. 8, 1991

[51] Int. Cl.5 ............................................. A61M 5/00
[52] U.S. Cl. .................... 604/191; 604/232; 604/205
[58] Field of Search .............. 604/82, 83, 85-90, 604/191, 192, 207, 213, 220, 232, 234, 236-238, 239, 240, 201, 205

[56] References Cited

U.S. PATENT DOCUMENTS

| | | | |
|---|---|---|---|
| 1,557,836 | 10/1925 | Hein | 604/237 |
| 3,659,587 | 5/1972 | Baldwin | 604/237 X |
| 3,696,806 | 10/1972 | Sausse | 604/191 X |
| 4,109,653 | 8/1978 | Kozan et al. | 604/191 |
| 4,738,660 | 4/1988 | Lucas | 604/139 |
| 4,755,169 | 7/1988 | Sarnoff et al. | 604/51 |
| 4,795,441 | 1/1989 | Bhatt | 604/124 |
| 4,902,281 | 2/1990 | Avoy | 604/191 |
| 5,067,948 | 11/1991 | Haber et al. | 604/213 |

Primary Examiner—John D. Yasko
Assistant Examiner—Adam J. Cermak
Attorney, Agent, or Firm—Townsend and Townsend

[57] ABSTRACT

A multiple cartridge syringe (2), especially useful for use in dispensing insulin, includes a body (4) housing first and second pharmaceutical-filled cartridges (30, 32). The cartridges are of the type with a septum (36) at one end (38) and a piston (42, 44) at the other end (40) with the liquid pharmaceutical (46, 48) between the two. The body also defines an accumulator chamber (10) within which an accumulator piston (26) is slidably mounted. The proximal end (12) of the body is open to provide access to the three pistons by a stem (22). When the cartridges are mounted within the body, the septums are pierced by hollow spikes (52, 53) which are connected to a flow path opening into the accumulator chamber. Check valves (58, 59) are used at the distal ends of the spikes to prevent liquid flow back into the cartridges. Pressing on the cartridge pistons forces the liquids into the accumulator chamber. Once the desired amounts of both liquids are in the accumulator chamber, the needle assembly is moved to its extended position which fluidly couples the needle to the accumulator chamber. The injection is given by driving the accumulators piston using the stem.

16 Claims, 6 Drawing Sheets

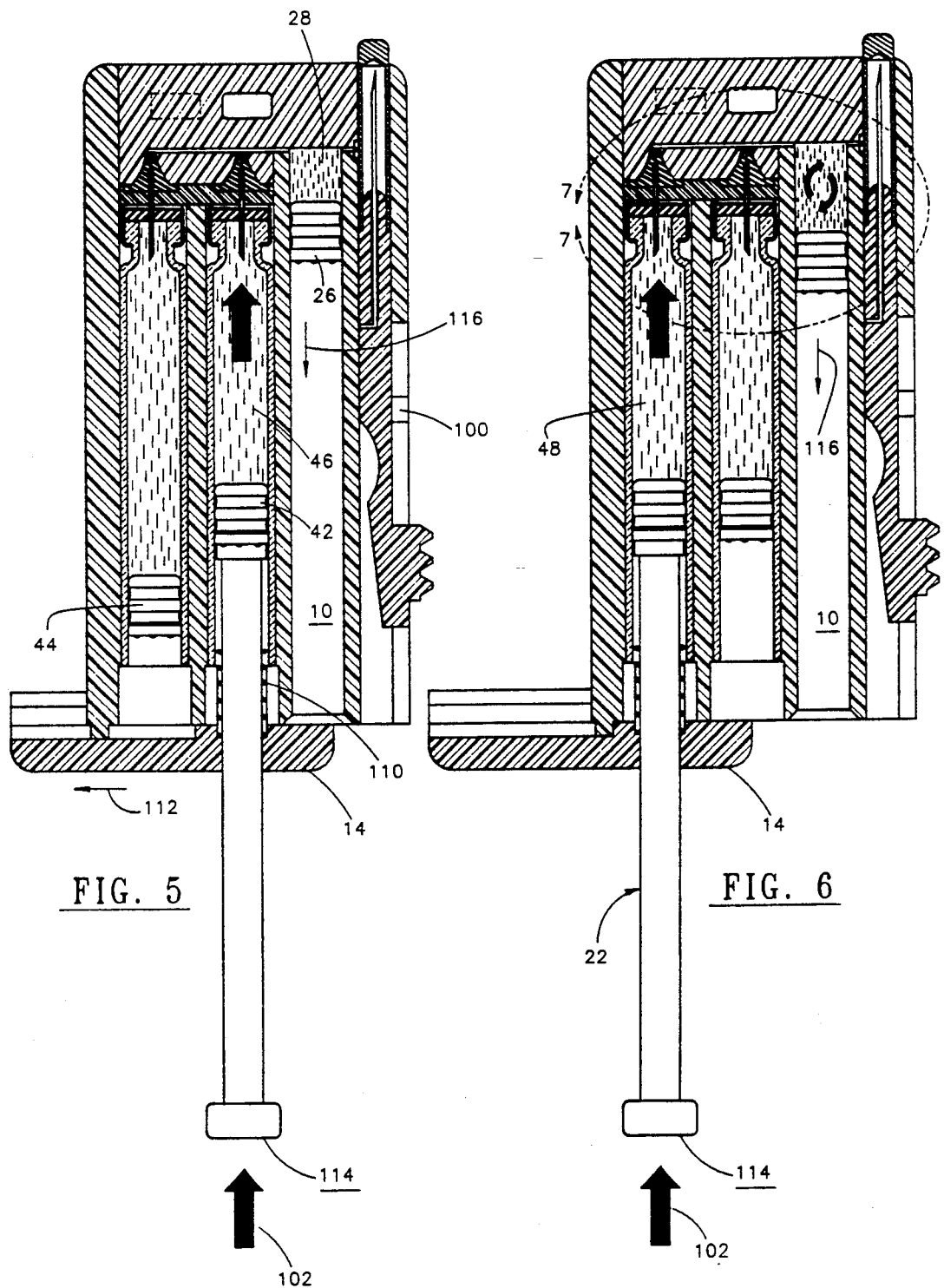

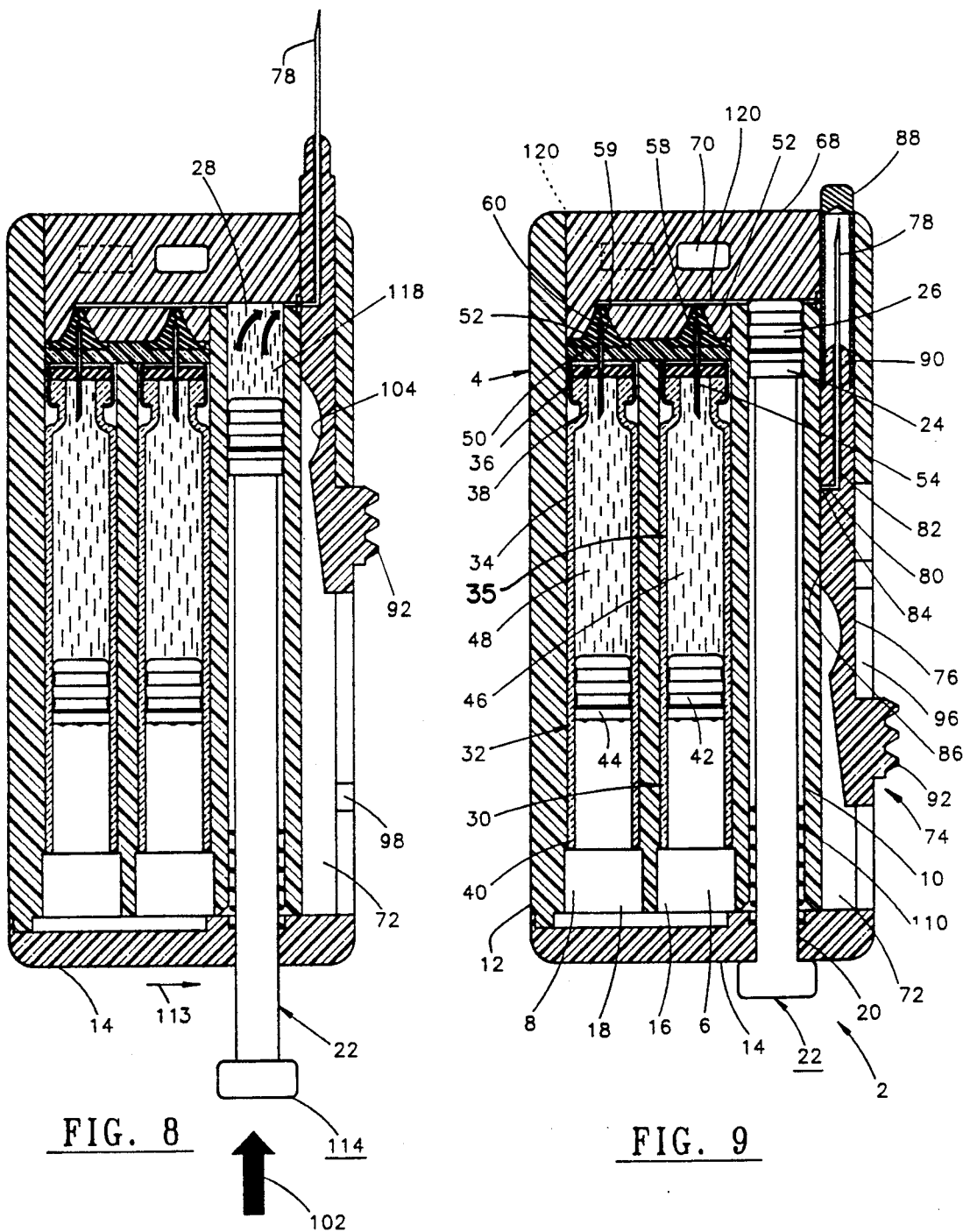

MULTIPLE CARTRIDGE SYRINGE

CROSS REFERENCE TO RELATED APPLICATIONS

This is related to U.S. patent application Ser. No. 07/668,878, titled MULTIPHARMACEUTICAL SYRINGE, the disclosures of which is incorporated by reference.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake, and expected activity. For example, insulin injected at the beginning of an active day may have more of the fast-acting insulin, while the insulin injection given at the end of the day before going to bed would likely have more intermediate- or long-acting insulin.

One of the problems with conventional insulin syringes is that they are designed to inject only one type of insulin, not a combination. Although insulin can be obtained as a mixture of the two types, the mixtures are generally a preset combination, such as 70% intermediate-acting and 30% fast-acting. Thus, the prior art limits the insulin user to a set mixture of the two insulins or the need to make two separate injections.

SUMMARY OF THE INVENTION

The present invention is directed to a syringe which uses two or more conventional pharmaceutical cartridges to allow the user to deliver desired amounts and proportions of each during a single injection from a common accumulator chamber. This permits, for example, an insulin user to select the amounts and proportions of two types of insulin delivered with a single injection.

The multiple cartridge syringe includes a body housing first and second pharmaceutical-filled cartridges. The cartridges preferably are of the type with a septum at one end, an exposed piston at the other and the liquid pharmaceutical between the two. The body also houses an accumulator chamber within which an accumulator piston is slidably contained. The proximal end of the body is open to provide access to the three pistons by a single stem. When the cartridges are mounted within the body, their septums are each pierced by hollow spikes. The hollow spikes are connected to a flow path which opens into the distal end of the accumulator chamber. Check valves are preferably used, typically at the distal ends of the spikes, to allow the pharmaceutical within the cartridges to flow out of the cartridge through the spike but not the reverse.

Pressing on the piston within a cartridge causes the pharmaceutical within the cartridge to flow through the spike, through the check valve, along the flow path and into the accumulator chamber. The pressure and increasing volume of the liquid within the accumulator chamber forces the accumulator piston away from the distal end of the accumulator chamber towards the proximal end of the body. Once the desired amounts of both liquid pharmaceuticals have been forced into the accumulator chamber and mixed therein, the piston stem is then inserted into the proximal end of the accumulator chamber to engage the accumulator piston.

The needle assembly is then fluidly coupled to the accumulator chamber. This is preferably accomplished by moving the needle assembly from its normally stored or retracted position to an extended position. This causes the distal end of the accumulator chamber to be fluidly coupled to the hollow needle. Pressing on the stem forces the newly-mixed liquids within the accumulator chamber through the hollow needle. Once the injection has been given, the needle assembly is moved back to its retracted position. This not only moves the needle to a safe position within the body, but also seals the needle from the accumulator chamber.

Preferably, a single stem is used to drive each of the pistons one-at-a-time. The stem can be retained by an end cap slidably mounted to the proximal end of the body. The end cap guides the stem as it pushes against the various pistons. After withdrawing the piston from the body, the end cap can be slid laterally to align the distal end of stem with a different piston.

A primary feature of the invention is that it permits a single injection of selected amounts and proportion of two or more liquid pharmaceuticals using a simple and compact syringe. In addition, the invention is designed to be usable with conventional pharmaceutical cartridges for reduced cost and enhanced flexibility. An insulin user is provided a flexible, convenient and compact syringe by which any desired proportion of insulins can be administered with a single injection.

Although the syringe as shown is a reusable design, it could easily be modified to be disposable by the user by preventing removal of the end cap and preventing removal of one or both of the spent pharmaceutical cartridges.

The accumulator piston can be made with a collapsible sterility skirt connected to the proximal end of the accumulator chamber. This will protect the sterility of the accumulator chamber during use and between uses.

The accumulator chamber is preferably sized to house substantially the entire stem when the syringe is not being used. This, plus an in-line arrangement of the cartridges and the accumulator chamber, allows the syringe to be quite compact and yet a relatively sturdy package. The preferred configuration of the syringe reduces or eliminates the stigma of abnormality created by the use of conventional hypodermic syringes and pharmaceutical vials.

Other features and advantages of the invention will appear from the following description in which the preferred embodiments have been set forth in detail in conjunction with the accompanying drawings.

BRIEF DESCRIPTION OF THE DRAWINGS

FIG. 5 is a cross-sectional view of the syringe of FIG. 4 with the end cap shifted and the plunger driving the first piston of the first cartridge forcing the first liquid into the accumulator chamber;

FIG. 6 shows the syringe of FIG. 5 with the end cap shifted to another position and the stem engaging the second piston of the second cartridge forcing the second liquid into the accumulator chamber where it mixes with the first liquid;

FIG. 8 shows the syringe of FIG. 6 with the end cap shifted back to the position of FIG. 4, the needle assembly in its extended position with the needle sheath removed, and the stem beginning to drive the accumulator piston to force the mixed liquid out of the accumulator chamber and through the hollow needle;

FIG. 9 shows the syringe of FIG. 8 following an injection with the needle assembly in the retracted positions;

DETAILED DESCRIPTION OF THE PREFERRED EMBODIMENTS

Figure 1:
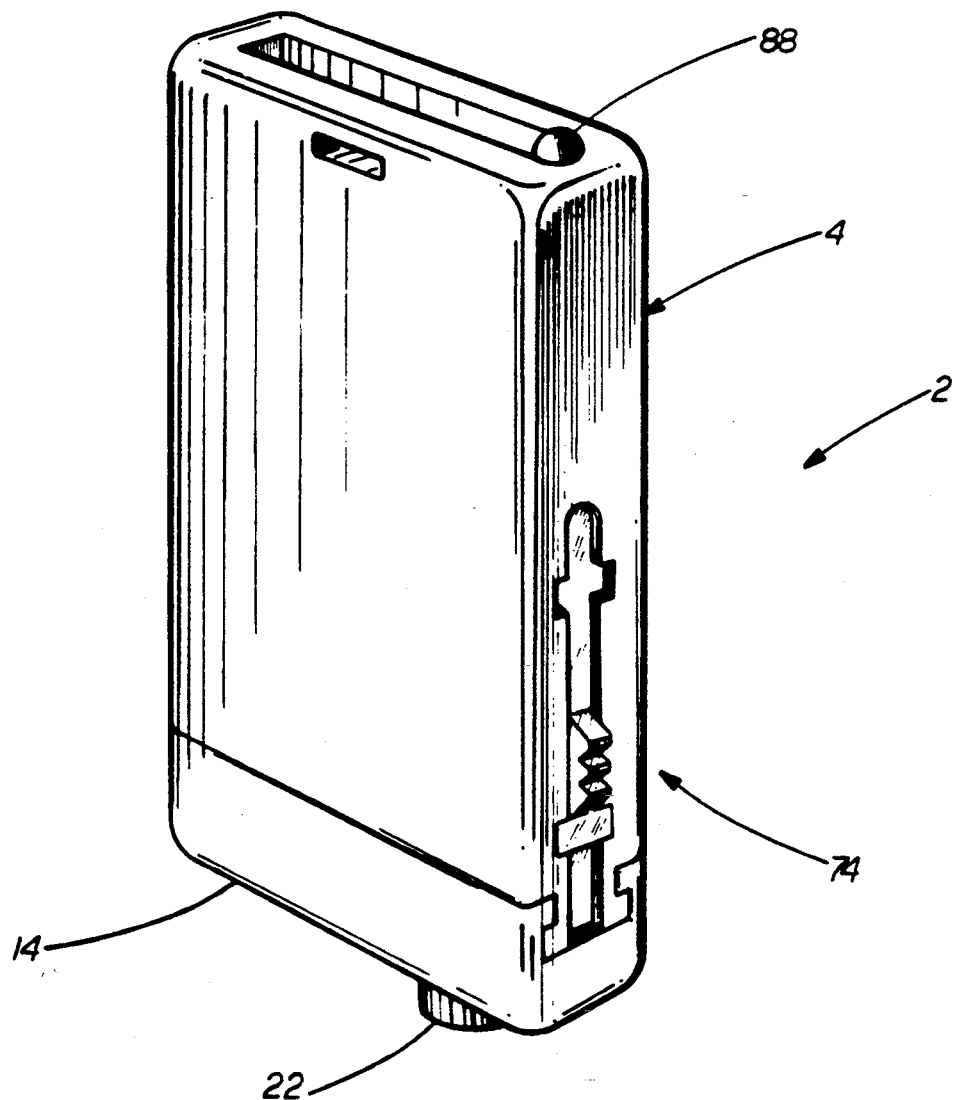
FIG. 1 is an isometric view of a syringe made according to the invention.
Figure 4:
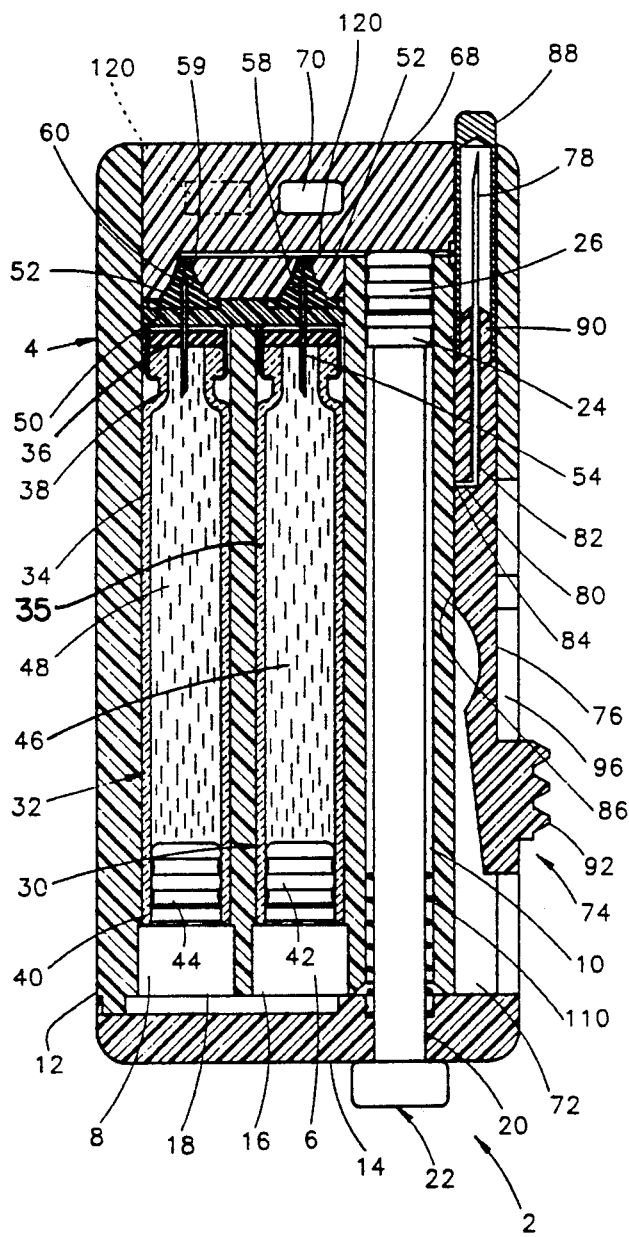
FIG. 4 is a cross-sectional view taken along line 4—4 of FIG. 2.
Figure 2:
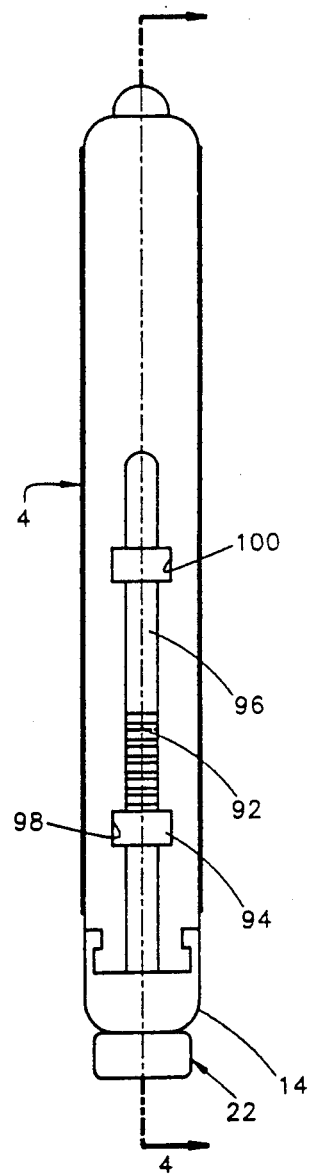
FIG. 2 is a side view thereof showing the position control button of the needle assembly.
Figure 3:
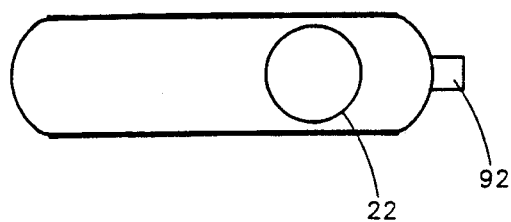
FIG. 3 is an end view thereof showing the finger engagement surface of the stem.

Referring the reader to FIGS. 1-3, a multiple cartridge syringe 2 is shown to include a body 4 defining first and second chambers 6, 8 and an accumulator chamber 10. Body 4 is made of a clear, pharmaceutically compatible plastic, such as polypropylene or acrylic. A proximal end 12 of body 4 is covered by a sliding end cap 14, thus covering the opened proximal ends 16, 18 of chambers 6, 8. End cap 14 has an opening 20 through which a stem 22 passes. As shown in FIG. 4, the distal end 24 of stem 22 is normally positioned adjacent a piston 26 mounted within accumulator chamber 10 at a distal end 28, see FIG. 5, of chamber 10.

Chambers 6, 8 are sized for receipt of first and second conventional pharmaceutical cartridges 30, 32. Cartridges 30, 32 each include a barrel 34, 35 having a pierceable septum 36 at a far end 38 and an opened near end 40. First and second cartridges 6, 8 include first and second pistons 42, 44 and contain first and second liquid pharmaceuticals 46, 48 between septums 36 and pistons 42, 44.

Figure 7:
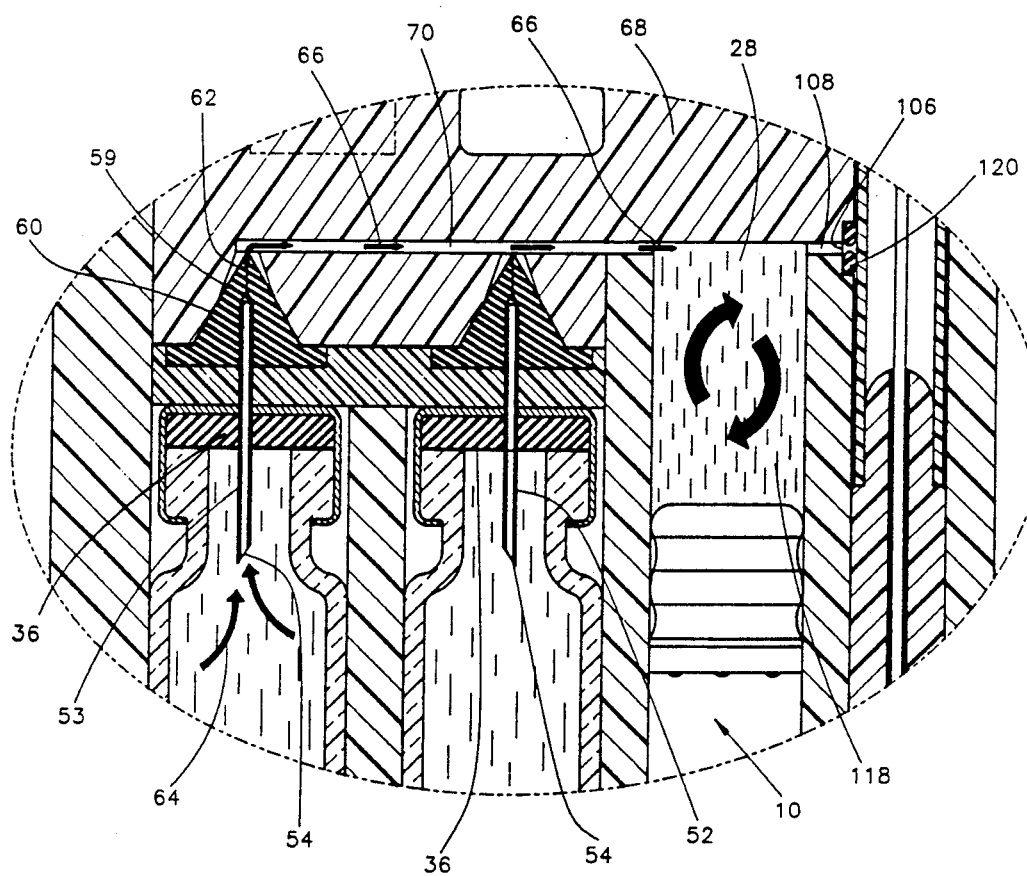
FIG. 7 is an enlarged view of a portion of the syringe of FIG. 6 taken along line 7—7.

The far ends 38 of first and second cartridges 30, 32 rest against a check valve support plate 50. Hollow spikes 52, 53 are mounted to and pass through support plate 50. Spikes 52, 53 have sharpened ends 54 which pierce septums 36 when cartridges 30, 32 are inserted into first and second chambers 6, 8. Slit conical check valves 58, 59, shown best in FIG. 7, are mounted to the outer ends 60 of spikes 52. Check valves 58, 59 have slits 62 which permit fluid to flow in the direction of arrows 64, 66 but not in the reverse direction. Valves 58 are preferably made of a firm elastomeric material, such as silicone rubber, such as sold by Dow Chemical Company of Midland, Michigan as Q4765.

Support plate 50 and check valves 58, 59 are retained in position by an end cap 68 permanently mounted to housing 4, such as with an adhesive. End cap 68 has a flow path 70 which provides fluid communication between the two check valves 58, 59 and distal end 28 of accumulator chamber 10.

Body 4 also includes a guide slot 72 having a rectangular cross-sectional shape. A needle assembly 74 is mounted for slidable movement within guide slot 72 and includes a needle carrier 76 to which a hollow needle 78 is mounted. An L-shaped bore 80 is formed in needle carrier 76 to connect the proximal end 82 of needle 78 to an orifice 84 along a flat side 86 of carrier 76. Needle assembly 74 also includes protective sheath 88 which is removably mounted to the outer end 90 of needle carrier 76 so to protect against contamination of needle 78 and inadvertent injury by the needle.

Needle carrier 76 includes a push button 92 having an enlarged end 94, see FIG. 2. Push button 92 is sized to move along a slot 96 while enlarged end 94 is sized to engage enlarged sections 98, 100 of slot 96. To move enlarged end 94 from enlarged section 98, as shown in FIGS. 2 and 4, to enlarged section 100, shown in FIG. 8, the user presses down upon push button 92 and slides needle assembly 74 in the direction of arrow 102 as shown in FIG. 8. An appropriate resilience is provided to needle carrier 76 by a cross-sectional decrease at 104 in the needle carrier. With needle carrier 76 in the extended position of FIG. 8, orifice 84, which opens into L-shaped bore 80, is aligned with an end 106 of a bore 108, thus fluidly coupling distal end 28 of accumulator chamber 10 to hollow needle 78.

To move stem 22 from the position of FIG. 4 to the position of FIG. 5, the user first withdraws stem 22 as far as possible from accumulator chamber 10. During the final movement of stem 22 from chamber 10, a coil spring 110 is compressed. End cap 14 is then moved in the direction of arrow 112. After stem 22 is no longer aligned with accumulator chamber 10, the user can release stem 22. Once stem 22 becomes aligned with first chamber 6, spring 110 automatically forces stem 22 into the first chamber, thus aiding proper axial alignment. The user then presses against the outer finger engaging surface 114 of stem 22 forcing first piston 42 in the direction of arrow 102. This causes first liquid 46 to flow through spike 52, check valve 58, flow path 70, and into distal end 28 of accumulator chamber 10. The fluid pressure of liquid 46 within chamber 10 causes accumulator piston 26 to move in the direction of arrow 116. Liquid 46 is not forced into second cartridge 32 due to the use of check valve 59.

After a sufficient amount of liquid 46 has been introduced into distal end 28 of chamber 10, stem 22 is then again withdrawn and cap 14 is again slid in the direction of arrow 112 until stem 22 becomes aligned with second chamber 8. The above process is repeated for second liquid 48 as shown in FIGS. 6 and 7 to create a mixed liquid 118 in distal end 28 of accumulator chamber 10.

Stem 22 is then withdrawn from second chamber 8 and end cap 14 is moved in direction of arrow 113 to the position of FIG. 8. Push button 92 is then depressed and needle assembly 74 is driven from the position of FIG. 6 to the position of FIG. 8. Protective sheath 88 is then removed and one end of the sheath is inserted into a blind storage hole 120 formed in end cap 68. The injection is given by pressing on surface 114 of stem 22 which causes the mixed liquid 118 to flow through bore 108, bore 80 and hollow needle 78.

Figures 10A, 10B:
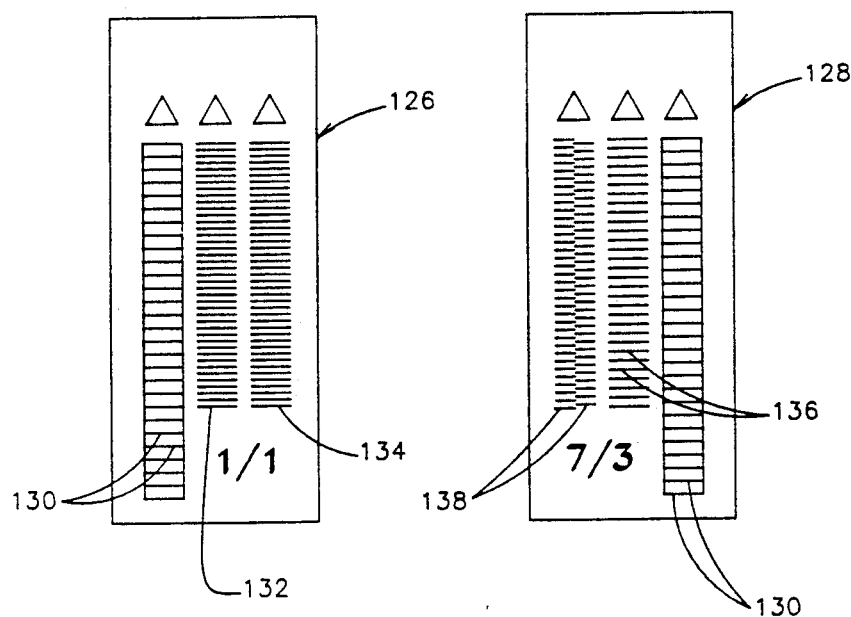
FIGS. 10A and 10B are front views of transparent dosage labels.

The amount of liquids 46, 48 forced into distal end 28 of accumulator chamber 10 can be gauged through the use of transparent dosage labels 126, 128 shown in FIGS. 10A and 10B. Label 126 includes accumulator calibrations 130. Labels 126, 128 are transparent except for the markings shown in FIGS. 10A and 10B to provide an unimpeded view of the contents of cartridges 30, 32 and accumulator chamber 10. The space between each calibration 130 equals one unit of medication. Label 126 also include first and second pharmaceutical calibrations 132, 134. Calibrations 132, 134 are each spaced apart by distances equal to one-half of a unit of medicine. Therefore, if the user moves pistons 42, 44 from one calibration 132, 134 to the next calibration 132, 134, equal amounts (one-half unit each) of liquids 46, 48 will be forced into accumulator chamber 10 to move piston 26 a distance equal to the distance between successive calibrations 130.

Label 128, mounted to the opposite side of body 4 as label 126, is used when the proportion of first liquid 46 to second liquid 48 is 7 to 3. The distance between successive first and second pharmaceutical calibrations 136, 138 corresponds to 70% of a unit and 30% of a unit respectively. Note that successive calibrations 138 are staggered—otherwise they could be too close together for easy reading. Labels 126, 128 are preferably removable so that labels having other calibrations for other mixture can be used as well.

Once the injection is complete, sheath 88 is removed from hole 120 and safely replaced over needle 78, button 92 is depressed to disengage enlarged end 94 from enlarged section 100, and needle 74 is brought back to its retracted position of FIGS. 4–6. Releasing push button 92 permits large end 94 to once again engage enlarged section 98 to keep the needle assembly from inadvertently being extended.

A fluid seal is provided at end 106 of bore 108 by an O-ring 124 as shown in FIG. 7. O-ring 124 engages the outer surface of sheath 88 when needle assembly 74 is in its retracted position of FIGS. 4–6 and presses against flat side 86 of needle carrier 76 in the region surrounding position 84 and the end of L-shaped bore 80 when in the extended position of FIG. 8. Instead of using a separate 0-ring, other types of seals, including a molded-in, outwardly extending ring seal, could be used. Also, to aid sterility, a check valve can be used adjacent 0-ring 124; this can be especially useful when a removable needle assembly is used.

The advantage of using blind hole 120 to temporarily house sheath 88 causes the sheath to extend laterally outwardly from the syringe during use. Thus, if the user inadvertently forgets to replace the sheath before withdrawing needle assembly back into guide slot 72, sheath 88 will immediately get in the way when the user attempts to store the syringe in the user's pocket, purse or carrying pouch. Also, if safety sheath 88 is not in place when pistons 42, 44 are depressed, liquid may leak through bore 108 and out guide slot 72. Thus, the user has an additional reason for properly maintaining safety sheath 88 in place.

For the convenience of the user, a through hole 122 can be provided through end cap 68 to permit syringe 2 to be carried, for example, on a keychain.

Figures 11A, 11B:
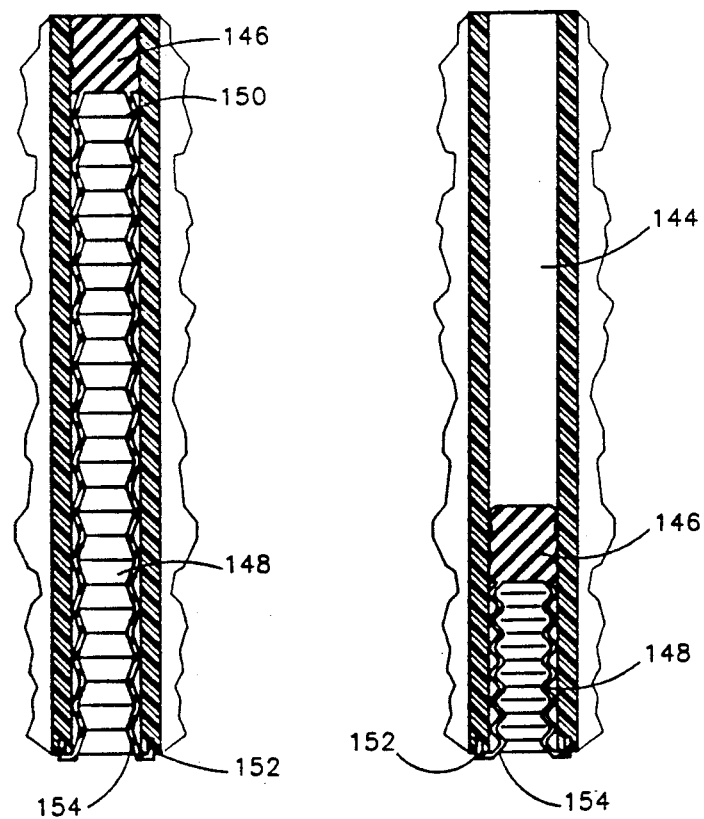
FIGS. 11A and 11B are simplified views showing the accumulator piston and chamber of FIGS. 4 and 5 used with a sterility skirt.

FIGS. 11A and 11B illustrate, in schematic form, an accumulator chamber 144 housing an accumulator piston 146 and a sterility skirt 148. Skirt 148 is a lightweight, fluid impervious, flexible tubular material, such as silicone rubber, secured to piston 146 at one end 150 of skirt 148 and to the proximal end 152 of chamber 144 at the other end 154 of skirt 148. Skirt 148 is in its extended condition of FIG. 11A when piston 146 is fully within chamber 144 and in its compressed condition of FIG. 11B when piston 146 is near proximal end 152. Therefore, skirt 148 and piston 146 to help keep the inner walls of chamber 144 sterile during use and between uses. Other methods for insuring sterility is maintained can be used as well.

Other modification and variation can be made to the disclosed embodiments without departing from the subject of the invention as defined in the following claims. For example, syringe 2 could be modified so that an empty, generally conventional cartridge is used as accumulator chamber 10. The needle assembly could be pivotally mounted to the syringe body. The needle assembly could also be permanently mounted in place or a separate needle assembly could be secured to the syringe body, such as with conventional twist-lock coupling. Instead of using check valves 58, 59, pistons 42, 44 could be made to be movable in one direction only, towards far end 38, to prevent the reverse flow of liquid back into the cartridges. The syringe could be made for use with more than two cartridges. The invention may also include an additional cartridge or chamber containing sterile saline solution useful for flushing out the hollow needle after an injection.

What is claimed is:

1. A syringe, for use with liquid-filled pharmaceutical cartridges of the type having a barrel, the barrel having an open end and an accessible end, a piston within the interior of the barrel and a liquid within the barrel between the piston and the accessible end, comprising:
   a body configured to house first and second of the cartridges therein;
   an elongate accumulator chamber;
   a movable accumulator piston housed within the accumulator chamber;
   first means, engageable with the accessible ends of the first and second cartridges, for fluidly coupling the interiors of the barrels of the first and second cartridges to the accumulator chamber;
   means for preventing fluid flow into the interiors of the barrels of the first and second cartridges;
   a hollow needle;
   means for selectively fluidly coupling the hollow needle with the accumulator chamber; and
   a stem engageable with the cartridge pistons and the accumulator piston by which selected amounts of liquid from the first and second cartridges are forcible by the stem into the accumulator chamber to mix within the accumulator chamber, the mixed liquid in the accumulator chamber being forcible by the stem through the selectively fluidly coupling means and through the hollow needle.

2. The syringe of claim 1 wherein the first fluidly coupling means include hollow spikes for piercing the accessible ends of the first and second cartridges.

3. The syringe of claim 1 wherein the fluid flow preventing means includes a one-way check valve for each of said first and second cartridges.

4. The syringe of claim 1 wherein the selectively fluidly coupling means includes a needle carrier mounted to the body for movement between an extended position and a retracted position.

5. The syringe of claim 4 wherein the selectively fluidly coupling means includes a first bore, formed within the body between the accumulator chamber and a first sealing position, and a second bore, formed within the needle carrier and fluidly coupling the hollow needle to a second sealing position, the first and second sealing positions being aligned when the needle carrier is in the extended position so to permit fluid flow between the accumulator chamber and the hollow needle, the first and second sealing positions being offset when the needle carrier is in the retracted position.

6. The syringe of claim 5 wherein the coupling means includes a removable needle sheath mounted to the needle carrier.

7. The syringe of claim 6 wherein the body includes a needle sheath storage element configured to mount the needle sheath, when removed from the needle carrier, to the body.

8. The syringe of claim 6 wherein the needle sheath includes an outer surface which covers the first sealing position when the needle carrier is in the retracted position so to seal the first bore.

9. The syringe of claim 5 wherein the accumulator chamber includes a distal end and a proximal end, the stem extendable from the proximal end.

10. The syringe of claim 9 wherein the first bore opens into the distal end of the accumulator chamber.

11. The syringe of claim 1 further comprising alignment means, movably mounted to the body, for selectively aligning the stem with the accumulator piston and with the pistons of the first and second cartridges.

12. The syringe of claim 11 wherein the alignment means includes an end cap slidably mounted to the body, the stem passing through the end cap, the stem having an outer end configured engagement by the user.

13. The syringe of claim 12 wherein the alignment means includes spring means for biasing the stem towards the body when the stem is substantially withdrawn from the body so to provide automatic biasing of the stem towards one of the pistons when the stem,.carried by the end cap, is aligned with soul one of the pistons.

14. The syringe of claim 1 wherein the body has portions constructed to enable the user to view the cartridges and the accumulator chamber.

15. The syringe of claim 14 further comprising calibration markings on said body to allow the user to gauge the amounts of liquids forced from the cartridges to the accumulator chamber.

16. A syringe for use with multiple pharmaceutical cartridges, the cartridges each having a hollow barrel, the barrel having an open end and a pierceable end, a piston mounted within the barrel, and a liquid housed within the interior of the barrel between the pierceable end and the piston, comprising:

a body having distal and proximal ends and defining first and second chambers sized for receipt of first and second of the cartridges, the first and second chambers being open at the proximal end of the body;

an elongate accumulator chamber formed within the body having a proximal end, open at the proximal end of the body, and a distal end;

an accumulator piston slidably mounted within the accumulator chamber;

first and second means for accessing the liquid within the first and second cartridges through the pierceable ends thereof;

a flow path fluidly coupling the first and second accessing means to the accumulator chamber;

means for preventing liquid flow from the accumulator chamber into the first and second cartridges;

a needle assembly, including a hollow needle, mounted to the body and movable between extended and retracted conditions;

means for fluidly coupling the accumulator chamber to the needle when the needle assembly is in the extended condition and for fluidly separating the accumulator chamber from the needle when the needle assembly is in the retracted condition; and a stem adapted for selectively engaging the piston of the first cartridge, the piston of the second cartridge and the accumulator piston so that liquid from the first and second cartridges can be forced into the accumulator chamber by the stem when the needle assembly is in the retracted condition to mix the liquid in the accumulator chamber and to force the accumulator piston towards the proximal end of the accumulator chamber, whereupon the mixed liquid in the accumulator chamber can be forced out through the hollow needle by the stem when the needle assembly is in the extended condition.

* * * * *